US008993334B2

(12) United States Patent
Torres

(10) Patent No.: US 8,993,334 B2
(45) Date of Patent: Mar. 31, 2015

(54) PROTEIN SEPARATION VIA ION-EXCHANGE CHROMATOGRAPHY AND ASSOCIATED METHODS, SYSTEMS, AND DEVICES

(71) Applicant: Anthony R. Torres, Centerville, UT (US)

(72) Inventor: Anthony R. Torres, Centerville, UT (US)

( * ) Notice: Subject to any disclaimer, the term of this patent is extended or adjusted under 35 U.S.C. 154(b) by 0 days.

(21) Appl. No.: 13/669,199

(22) Filed: Nov. 5, 2012

(65) Prior Publication Data
US 2013/0164827 A1 Jun. 27, 2013

Related U.S. Application Data

(63) Continuation of application No. 12/619,421, filed on Nov. 16, 2009, now Pat. No. 8,304,248.

(51) Int. Cl.
C07K 1/36 (2006.01)
C07K 1/18 (2006.01)
C07K 1/00 (2006.01)

(52) U.S. Cl.
CPC .... C07K 1/18 (2013.01); C07K 1/36 (2013.01)
USPC .............. 436/86; 435/183; 435/212; 435/219

(58) Field of Classification Search
CPC ............... C07K 1/36; C07K 1/18; C07K 1/00
USPC ............................. 436/86; 435/183, 212, 219
See application file for complete search history.

(56) References Cited

U.S. PATENT DOCUMENTS 5,028,696 A * 7/1991 Torres et al. ............... 530/388.1
5,284,933 A 2/1994 Dobeli et al.
5,310,663 A 5/1994 Dobeli et al.
5,439,591 A 8/1995 Pliura et al.
5,545,328 A 8/1996 Pliura et al.
5,719,060 A 2/1998 Hutchens et al.
5,788,845 A 8/1998 Jepsson (Continued)

FOREIGN PATENT DOCUMENTS

WO WO 03/044043 5/2003

OTHER PUBLICATIONS

Bachi et al.; "Performance of combinatorial Peptide Libraries in Capturing the Low-Abundance Proteome of Red Blood Cells. 2. Behavior of Resins Containing Individual Amino Acids"; Anal. Chem. 2008, 80; 3557-3558.

(Continued)

Primary Examiner — Christine T Mui

(57) ABSTRACT

The present invention provides methods for separating proteins from a protein mixture. In one aspect, a method for separating a high concentration protein mixture into a bound protein fraction and a flow-through protein fraction can include delivering a protein mixture through an ion exchange column at a fixed pH and a fixed salt concentration. The fixed pH and the fixed salt concentration have been preselected to cause separation of the protein mixture into a bound protein fraction and a flow-through protein fraction. In this case, the bound protein fraction binds to the ion exchange column and the flow-though protein fraction flows though the ion exchange column. The method can further include receiving the flow-through protein fraction from the ion exchange column separate from the bound protein fraction, wherein either the bound protein fraction or the flow-through fraction contains a protein of interest.

20 Claims, 2 Drawing Sheets

(56) References Cited

U.S. PATENT DOCUMENTS

| | | |
|---|---|---|
| 6,056,951 A | 5/2000 | Torres |
| 6,177,278 B1 | 1/2001 | Haj-Ahmad |
| 6,225,047 B1 | 5/2001 | Hutchens et al. |
| 6,291,248 B1 | 9/2001 | Haj-Ahmad |
| 6,579,719 B1 | 6/2003 | Hutchens et al. |
| 6,818,411 B2 | 11/2004 | Hutchens et al. |
| 7,026,453 B2 | 4/2006 | Haj-Ahmad |
| 7,138,120 B2 | 11/2006 | Laursen et al. |
| 7,186,410 B2 | 3/2007 | Chtourou et al. |
| 7,323,553 B2 | 1/2008 | Fahmer et al. |
| 7,396,468 B2 | 7/2008 | Boyes et al. |
| 7,431,842 B2 | 10/2008 | Haj-Ahmad |
| 7,531,645 B2 | 5/2009 | Basey et al. |
| 2007/0055055 A1 | 3/2007 | Sang et al. |
| 2007/0161120 A1 | 7/2007 | Lopez-Avila |

OTHER PUBLICATIONS

Egisto Boschetti et al.; "The art of observing rare protein species in proteomes with peptide ligand libraries"; Proteomics 2009, 9, 1492, 1500-1501.

Norgen Bioteck Corporation, ProteoSpin Abundant Serum Protein Depletion Kit, Product #17300, Product Insert. 2007. 5 pages.

* cited by examiner

PROTEIN SEPARATION VIA ION-EXCHANGE CHROMATOGRAPHY AND ASSOCIATED METHODS, SYSTEMS, AND DEVICES

PRIORITY DATA

This application is a continuation application of U.S. patent application Ser. No. 12/619,421, filed Nov. 16, 2009, now issued as U.S. Pat. No. 8,304,248.

FIELD OF THE INVENTION

The present invention relates to the separation and/or isolation of proteins from a protein mixture. Accordingly, the present invention involves the fields of medical diagnostics and biochemistry.

BACKGROUND OF THE INVENTION

The search for disease biomarkers has created a demand for rapid protein analysis from serum, plasma, and other complex protein mixtures. Several separation modalities, including chromatography, electrophoresis, isoelectric-focusing, and mass spectrometry are used in the search for biomarkers for numerous disease states.

Serum and plasma, for example, contain a rich source of biomolecules including a complex mixture of proteins. It is believed that many proteins, including newly synthesized proteins and especially degraded protein fragments, are transported in blood. Because of this, the concentration of newly synthesized proteins or proteins that are being degraded may vary depending on circumstances. This can be especially true in some disease states, thus potentially allowing diagnosis of such diseases through the presence of certain biomarkers. Serum, however, presents challenges for the physical detection of such proteins as they are present at substantially lower concentrations as compared to high abundant proteins. Of the thousands of proteins that are present in blood, only a handful make up a vast majority of the total protein mass in serum. Thus these "high abundant" proteins can cause interference problems with most if not all protein separation methods.

One exemplary method that is often utilized to remove two of the high abundant proteins from serum, namely albumin and IgG, is based on immunoaffinity chromatography. These affinity columns contain immobilized antibodies against human albumin and IgG that function to bind these proteins. The remainder proteins that do not, in theory, bind to the antibodies in the affinity column are retrieved in a pass-through fraction. This method of extraction can be expensive and inefficient, as only small amounts of serum (e.g. less than 50 µl) can be depleted of albumin and IgG on small columns (1 ml or less).

SUMMARY OF THE INVENTION

The present invention provides methods for separating proteins from a protein mixture. In one aspect, for example, a method for separating a high concentration protein mixture into a bound protein fraction and a flow-through protein fraction includes delivering a protein mixture through an ion exchange column at a fixed pH and a fixed salt concentration. The fixed pH and the fixed salt concentration have been preselected to cause separation of the protein mixture into a bound protein fraction and a flow-through protein fraction. Thus, the bound protein fraction binds to the ion exchange column and the flow-though protein fraction flows though the ion exchange column. The method further includes receiving the flow-through protein fraction from the ion exchange column and then subsequently eluting the bound protein fraction from the column and thus receiving the bound protein fraction separate from the flow-through fraction. Additionally, either the bound protein fraction or the flow-through fraction contains a protein of interest. Accordingly in one aspect, the protein of interest is in the flow-through protein fraction. In another aspect, the protein of interest is in the bound protein fraction.

Various protein mixtures are contemplated for use with the methods according to aspects of the present invention. For example, in one aspect, the protein mixture is a biological fluid. Non-limiting examples of biological fluids can include blood serum, blood plasma, urine, CNS fluid, saliva, cellular extracts, tissue culture extracts, and mixtures thereof. Additionally, the protein mixture can be utilized in a variety of forms. For example, in one aspect the protein mixture is an undiluted biological fluid. In another aspect, the protein mixture is a non-dialyzed biological fluid. In yet another aspect, the protein mixture is a non-ultafiltrated biological fluid. Furthermore, a biological fluid can be treated prior to separation. Non-limiting examples of such treatments include reducing agents, protease enzyme treatments, carbohydrate modifications, detergents, urea, and combinations thereof.

The methods of the present invention can be used to process large volumes of protein mixtures as compared to the capacities of the ion exchange columns being utilized. In one aspect, for example, the ion exchange column has a protein capacity that is at least the same as the total protein in an undiluted protein mixture. In another aspect, the ion exchange column has a protein capacity that is at least 5 times smaller than the total protein in an undiluted protein mixture. Additionally, in one aspect the high concentration protein mixture has a protein concentration that is at least 10% greater than ion exchange column protein capacity. In another aspect, the high concentration protein mixture has a protein concentration that is at least 20% greater than the ion exchange column protein capacity.

The ion exchange columns according to aspects of the present invention can include anion exchange columns or cation exchange columns. Additionally, a variety of fixed pH values can be used when separating a high concentration protein mixture into a bound protein fraction and an unbound protein fraction. For example, in one aspect the fixed pH is from about 2.0 to about 10.0. In another aspect, the fixed pH is from about 8.0 to about 10.0. In yet another aspect, the fixed pH is from about 2.0 to about 6.0.

In another aspect of the present invention, a method for separating a protein mixture into a bound protein fraction and a flow-through protein fraction is provided. Such a method can include delivering a protein mixture through an ion exchange column at a fixed pH and a fixed salt concentration, where the fixed pH and the fixed salt concentration have been preselected to cause separation of the protein mixture into a bound protein fraction that binds to the ion exchange column and a flow-through protein fraction that flows through the ion exchange column, and where greater than or equal to about 5% of protein in the protein mixture is in the flow through fraction. The method also includes receiving the flow-through protein fraction from the ion exchange column separate from the bound protein fraction, and wherein either the bound protein fraction or the flow-through fraction contains a protein of interest.

In yet another aspect of the present invention, a method for isolating a high abundant protein from a high concentration protein mixture is provided. Such a method includes delivering a high concentration protein mixture through an ion exchange column at a fixed pH and a fixed salt concentration, wherein the fixed pH and the fixed salt concentration have been preselected to cause separation of the protein mixture into a bound protein fraction and a flow-through protein fraction. The bound protein fraction binds to the ion exchange column and the flow-though protein fraction flows though the ion exchange column, and, in this case, a majority of the high abundant protein is in the bound protein fraction. The method also includes receiving the flow-through protein fraction from the ion exchange column and subsequently eluting the bound protein fraction including the majority of the high abundance protein from the ion exchange column.

A variety of high abundant proteins are contemplated, and it should be noted that any protein that is in high abundance in a protein mixture should be seen as being within the present scope. In one aspect, however, non-limiting examples can include transferrin, immunoglobulins, albumin, and combinations thereof.

The fixed pH and fixed salt concentration can vary depending on the high abundance proteins being separated and the nature of the protein mixture. In one aspect, however, the fixed pH is from about 2.0 to about 10.0 and the fixed salt concentration is from about 2 mM to about 400 mM. In another aspect, the fixed pH is from about 5.2 to about 8.2 and the fixed salt concentration is from about 20 mM to about 300 mM.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention.

DETAILED DESCRIPTION

Figure 1:
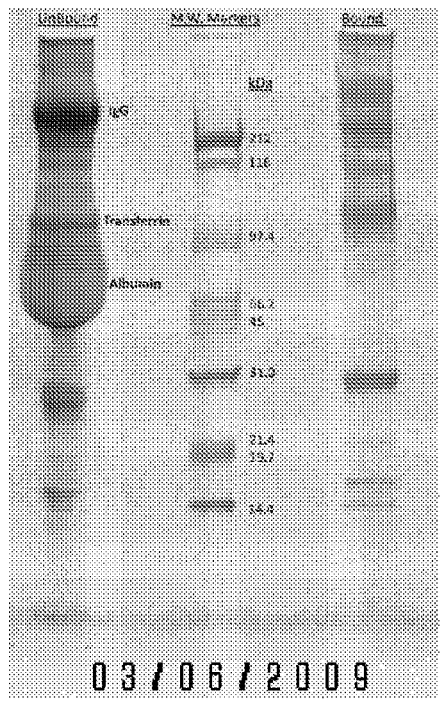
FIG. 1 is an image showing protein separation after dialysis by 1-dimensional SDS gel electrophoresis according to one aspect of the present invention.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a protein" includes one or more of such proteins, and reference to "the column" includes reference to one or more of such columns.

DEFINITIONS

In describing and claiming the present invention, the following terminology will be used in accordance with the definitions set forth below.

As used herein, the term "high abundance protein" refers to proteins that make up greater than about 5 wt % of a protein mixture.

As used herein, the term "high concentration protein mixture" refers to a protein mixture that has a protein concentration that is equal to or higher than the protein capacity of an ion-exchange column through which such a protein mixture is passed.

As used herein, the term "affinity binding" refers to binding between a protein and a substrate that is not a result of an ion-exchange interaction.

As used herein, the term "protein capacity," when referring to an ion-exchange column, refers to the amount of protein that is capable of binding to the column.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

In the practice of protein ion-exchange chromatography, proteins can be eluted from an ion-exchange column by an increase in salt concentration (e.g. NaCl) or a change in pH. In a typical procedure, a protein mixture is run through a column such that essentially all of the protein in the mixture is bound to the column. In such cases, only small amounts of a protein mixture can be processed to allow all of the protein in the sample to bind to the column. Binding is followed by an increase in salt concentration or a decrease in pH to elute the proteins from the column. The increase in salt or decrease in pH is usually performed as a gradient change to allow sufficient protein separation to occur. This protein separation scheme can be hampered, however, by the presence of high abundance proteins such as albumin, transferrin, IgG, and the like. These high abundance proteins can impede the separation and/or the identification of low abundance proteins from the protein mixture.

The inventor has discovered that proteins from a protein mixture can be separated without having total binding of all of the proteins in a protein mixture to the column. In this case, proteins are separated into a bound fraction that binds to the column and a flow-through fraction that flows though the column prior to elution. As such, this process produces a meaningful separation of proteins, namely, the proteins are separated into bound and flow-through fractions as compared to traditional separation processes whereby essentially all of the protein in a protein sample is bound to the column and salt and/or pH gradients cause protein separation as proteins are eluted off the column. As such, one significant benefit of the methods according to aspects of the present invention pertains to the amount of protein that can be separated. In this case, high abundance proteins can be separated from lower abundance proteins in much higher concentrations of protein mixtures than is possible with traditional ion-exchange methods.

Accordingly, in one aspect, a method for separating a high concentration protein mixture into a bound protein fraction and a flow-through protein fraction is provided. Such a method includes delivering a protein mixture through an ion exchange column at a fixed pH and a fixed salt concentration, wherein the fixed pH and the fixed salt concentration have been preselected to cause separation of the protein mixture into a bound protein fraction and a flow-through protein fraction. Thus the bound protein fraction binds to the ion exchange column and the flow-though protein fraction flows though the ion exchange column such that the flow-through protein fraction is received and collected as it flows through the ion exchange column while the bound protein fraction remains bound to the column. The bound protein fraction is then eluted from the column and is received and collected separately from the flow-through protein fraction. Additionally, either the bound protein fraction or the flow-through fraction can contain a protein of interest. It should be noted that, in one aspect, the present techniques encompass ion-exchange binding of protein to adsorbent, and that such binding is not a result of affinity binding.

In another aspect of the present invention, a method for separating a protein mixture into a bound protein fraction and a flow-through protein fraction is provided. The protein mixture can contain protein of any concentration, including those protein mixtures defined as high concentration protein mixtures. The method includes delivering a protein mixture through an ion exchange column at a fixed pH and a fixed salt concentration, where the fixed pH and the fixed salt concentration have been preselected to cause separation of the protein mixture into a bound protein fraction that binds to the ion exchange column and a flow-through protein fraction that flows through the ion exchange column, and where greater than or equal to about 5% of protein in the protein mixture is in the flow through fraction. The method also includes receiving the flow-through protein fraction from the ion exchange column and subsequently eluting and receiving the bound protein fraction separately from the flow-through fraction. A protein of interest can be contained either the bound protein fraction or the flow-through fraction. In another aspect, greater than or equal to about 25% of protein in the protein mixture is in the flow through fraction. In yet another aspect, greater than or equal to about 50% of protein in the protein mixture is in the flow through fraction. In a further aspect, greater than or equal to about 75% of protein in the protein mixture is in the flow through fraction.

Many of the high abundance proteins in a typical serum/plasma mixture have high isoelectric points (pI) and/or low affinities to anion-exchange absorbents. Standard chromatography protocols dictate that conditions should be set for all proteins to bind to the column, thus necessitating higher pH conditions (e.g. >7.0). As an example, immunoglobulin proteins generally have isoelectric points above pH 6.5. As such, a majority of immunoglobulins can be made to flow through the column by lowering the buffering conditions on the column and of the protein mixture to below pH 6.5. In such a situation, the majority of immunoglobulins will not bind to the column and will thus be present in the flow-through fraction. Processing such a protein mixture at even lower pH conditions will lower the affinity of immunoglobulins to the column even lower, thus increasing the amount of immunoglobulin that passes through the column in the flow-through fraction.

As another example, albumin is a high abundance protein that can pass through an ion-exchange column under the proper conditions. Although albumin has a pI of about pH 4.5, this protein does not bind well to anion-exchange columns, possibly due to structural constrains of such proteins. As one non-limiting example, lowering the buffering concentration conditions of the column and of the protein mixture to about pH 6.2 in about 20-150 mM NaCl will allow a majority of albumin proteins to flow through the column. It should be noted that albumin, transferrin, and immunoglobulin proteins are categorizations that can represent different protein species. The pI properties of immunoglobulin proteins made by different B-cells create variability. Albumin binds many different small molecules that create pI variability and column-binding characteristics as well. Additionally, transferrin can display different column affinity depending on the presence or absence of iron molecules.

By setting column and protein mixture conditions to a pH that is lower than 6.5, and increasing the NaCl concentration, the high abundance proteins (e.g. immunoglobulin, transferrin, albumin, fibrinogen, and the like) can be separated from lower abundance proteins on small ion-exchange columns. Surprisingly large volumes of protein can be processed using such small ion-exchange columns. For example, an anion-exchange column containing about 100 µl of DEAE-cellulose can allow for the processing of greater than 1 ml of undiluted serum protein mixture such that the low abundance proteins bind to the column and the high abundance proteins flow through the column. If a protein of interest is in the bound protein fraction, the column can be eluted by lowering pH further or by increasing the salt concentration.

If, for example, the high abundance proteins made up 75% of the proteins in the protein mixture, and conditions were set so that the high abundance proteins flow through, then only about 25% of proteins in the mixture will bind to the column. Thus if the conditions are set to cause the high abundance proteins to flow through, and the remaining proteins in the protein mixture are less than the binding capacity of the column, then substantially all of these remaining proteins should bind to the column, provided they are capable of binding given the conditions. If there are more remaining proteins in the protein mixture than the binding capacity of the column, then a portion of the remaining proteins will flow through the column as the binding capacity is reached.

In another aspect, a weak or strong cation-exchange absorbant can be used. Non-limiting examples include CM-cellulose, sulfoethyl cellulose, and the like. Additionally, more rigid agarose or polymeric adsorbents can also be used. The use of cation-exchange adsobants generally is benefited from the use of lower pH buffering conditions (e.g. from about pH 4.5 to about pH 6.0) in low salt conditions (e.g. from about 5 mM to about 154 mM). At these conditions, proteins with a high pI such as immunoglobulins, transferrin, fibrinogen, and the like, bind with high affinity to the negatively charged adsorbent. This thus allows for the binding of high abundance proteins to the column and the collection of unbound low abundance proteins from the flow-through fraction. One benefit of such a technique may be the further separation of proteins previously separated using an anion-exchange process, or if a protein of interest has a high pI.

Various protein mixtures are contemplated for separation according to the aspects of the present invention, and any protein mixture capable of such separation should be considered to be within the present scope. In one aspect, for example, the protein mixture can be a biological fluid. Non-limiting examples of biological fluids can include blood serum, blood plasma, urine, CNS fluid, saliva, cellular extracts, tissue culture extracts, and the like. In one specific aspect, the biological fluid can be serum or plasma.

One benefit of the present techniques for protein separation is the ability to process protein mixtures via ion-exchange chromatography that contain high concentrations of protein. In many aspects, for example, the protein mixture can be an undiluted biological fluid. In traditional ion-exchange procedures, a protein sample is heavily diluted in order to reduce the protein concentration in the sample to a level that allows all of the protein to bind to the column. The present methods allow an undiluted protein mixture, such as an undiluted biological fluid, to be processed via ion-exchange chromatography in order to ascertain the presence of a protein of interest, separate high abundance proteins, etc. It should be noted that the addition of column buffer to a protein mixture should not necessarily be considered dilution. For example, a 5 ml whole serum sample processed on a column is not considered "diluted" by the addition of 5 ml of column buffer to facilitate movement through the column because 5 ml of serum is still loaded on the column regardless of the buffer. It should also be noted that in some aspects the protein mixture can be diluted to lower the salt concentration to levels below normal saline (154 mM NaCl).

It can be beneficial, however, to remove from biological fluids tissue, cells, or other large biological matter that can hamper the ion-exchange process. Biological fluids derived from blood, for example, can be allowed to clot to remove blood cells therefrom. It should be noted, however, that the present scope should not be limited to undiluted biological fluids, and that some level of dilution may be beneficial, depending on the specific ion-exchange conditions and the proteins being separated.

In another aspect of the present invention, the protein mixture can be a non-dialyzed biological fluid. Protein mixtures can be processed according to the present techniques in a non-dialyzed, a substantially non-dialyzed, or a dialyzed state. Traditional approaches to ion-exchange chromatography exhaustively dialyze a biological sample such as serum prior to processing. The present techniques allow a biological fluid to be processed at physiological salinity levels. Of course, the salinity can be increased or decreased relative to physiological conditions, depending on the protein of interest and the particular protocol being performed. It should also be noted that in some aspects the protein mixture can be dialyzed.

Certain procedures are compatible with higher salt concentrations, and in such cases, high salt protein mixtures can be separated and subsequently processed. Non-limiting examples of such procedures can include size exclusion chromatography, immobilized metal affinity chromatography, hydrophobic interaction chromatography, and the like. Certain procedures are facilitated with lower salt concentrations, and as such, flow-through fractions and/or bound fractions can be dialyzed or ultrafiltrated following protein separation. Non-limiting examples of such procedures can include one-dimensional polyacrylamide gel electrophoresis, other electrophoresis procedures such as iso-electrofocusing, 2-dimensional gel electrophoresis, and the like.

In yet another aspect, the protein mixture can be a non-ultafiltrated biological fluid. Ultrafiltration is known in the art, and is a technique that is typically used in traditional ion-exchange chromatography approaches. The present techniques allow the processing of protein mixtures that have not been filtered to such an extent, and thus can allow an increased protein separation performance, as well as decreased protein separation time. It should be noted, however, that the present scope also includes the processing of protein mixtures that have been substantially non-ultrafiltrated, as well as those that have been ultrafiltrated. Additionally, as is discussed above, it can be beneficial to remove cellular material, tissue, and other debris from the protein mixture in order to avoid clogging the column. Such a removal can be accomplished by filtration of the protein mixture, and such filtration should not be seen as ultrafiltration.

A protein mixture such as a biological fluid can additionally be treated prior to or during ion-exchange chromatography in order to modify a protein or proteins contained therein. Such modifications can be used to enhance the separation procedure, to facilitate future processing steps to be performed on proteins of interest, to facilitate protein identification, and the like. Non-limiting examples of such treatments can include reducing agents, protease enzyme treatments, detergent addition, urea, carbohydrate modifications, and the like.

As has been described, the pH of the column during separation can influence the collection of proteins in the flow-through fraction vs. the proteins in the bound fraction. Thus the fixed pH can be within a number of pH ranges, depending on the desired protein separation, the protein of interest, and whether or not it is intended for the protein of interest to be in the bound fraction or the flow-through fraction. As such, any fixed pH can be within the present scope, depending on these factors. In one aspect, for example, the fixed pH can be from about 2.0 to about 10.0. In another aspect, the fixed pH can be from about 8.0 to about 10.0. In yet another aspect, the fixed pH can be from about 2.0 to about 6.0.

One useful benefit of the present techniques is the ability to process quantities of protein that are much higher than the traditional loading capacities of ion-exchange columns. Thus, because all protein in a sample is not required to bind to the column, very high concentrations of protein in a protein mixture can quickly be separated using these techniques. For example, in one aspect, the ion exchange column has a protein capacity that is at least the same as the total protein in an undiluted protein mixture. As such, a protein mixture having total protein content that is at least the same as the protein capacity of a given ion-exchange column can be processed using the present techniques. In another aspect, the ion exchange column has a protein capacity that is at least 5 times smaller than the total protein in an undiluted protein mixture. Similarly, a protein mixture having a total protein content that is at least 5 times the protein capacity of a given ion-exchange column can be processed using the present techniques. In yet another aspect, a high concentration protein mixture has a protein concentration that is at least 10% greater than the ion exchange column protein capacity. In another aspect, a high concentration protein mixture has a protein concentration that is at least 20% greater than the ion exchange column protein capacity.

As has been described, the present techniques can additionally be useful for the removal of high abundance proteins from a protein mixture. In one aspect, for example, a method for isolating a high abundant protein from a high concentration protein mixture is provided. Such a method can include delivering a high concentration protein mixture through an ion exchange column at a fixed pH and a fixed salt concentration, where the fixed pH and the fixed salt concentration have been preselected to cause separation of the protein mixture into a bound protein fraction and a flow-through protein fraction. In this case, the bound protein fraction binds to the ion exchange column and the flow-though protein fraction flows though the ion exchange column. Thus, the fixed pH and the fixed salt concentration are set to allow a majority of the high abundant protein to be bound to the column. The flow-through fraction can be received from the ion exchange column separate from the bound protein fraction, and the bound protein fraction, including the majority of the high abundance protein, can be eluted from the ion exchange column.

The ranges within which the fixed pH and fixed salt concentrations are located can vary, depending on the conditions of the separation protocol and the particular high abundance proteins being bound to the column. In one aspect, for example, the fixed pH is from about 2.0 to about 10.0 and the fixed salt concentration is from about 2 mM to about 400 mM. In another aspect, the fixed pH is from about 5.2 to about 8.2 and the fixed salt concentration is from about 20 mM to about 200 mM. It should be noted that, in one aspect, the ion-exchange column is a cation exchange column. Similarly, in some aspects the ion-exchange column can be an anion exchange column. It should also be noted that the bound protein fraction is bound to the column by ionic charges as opposed to affinity binding.

EXAMPLES

Example 1

Figure 2:
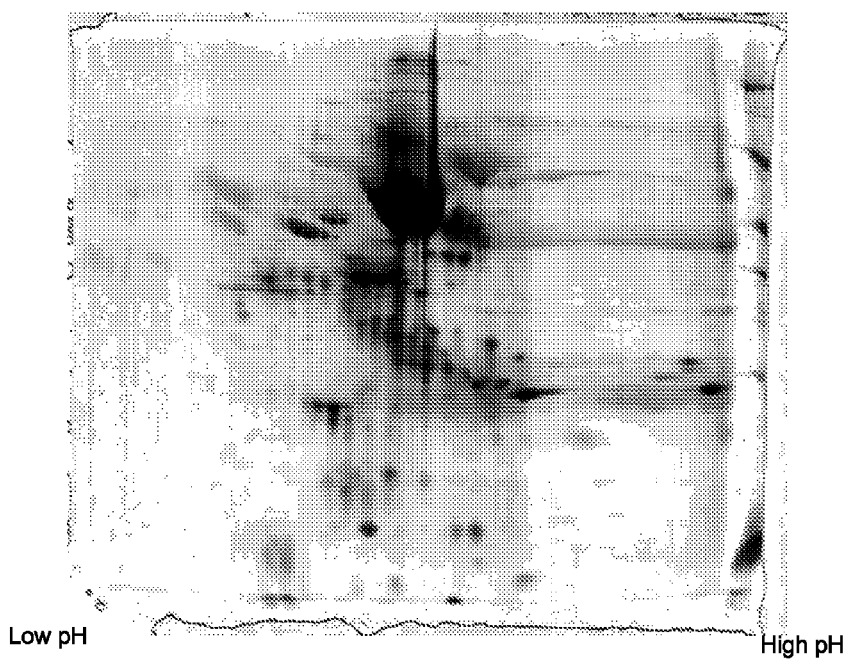
FIG. 2 is an image showing unbound protein separation after dialysis by 2-dimensional gel electrophoresis according to another aspect of the present invention.
Figure 3:
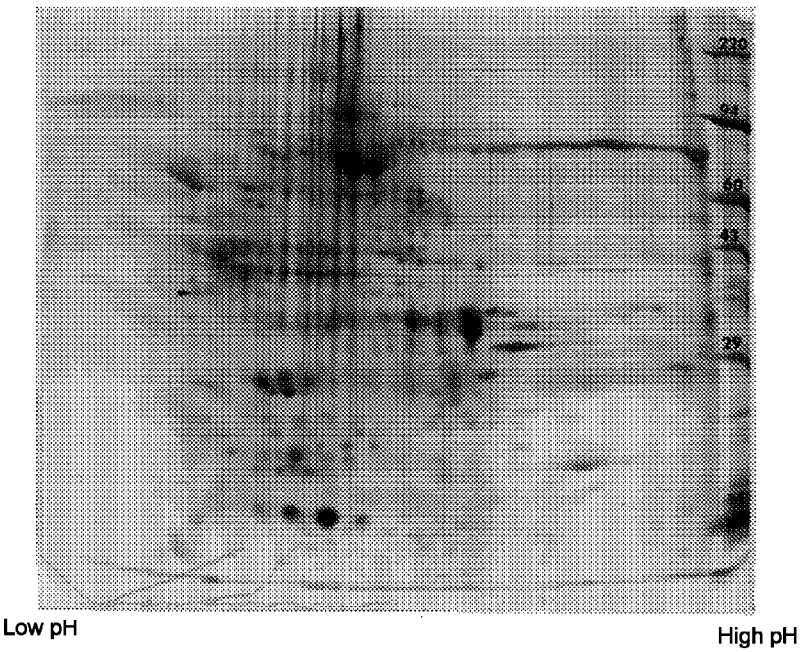
FIG. 3 is an image showing bound protein separation by 2-dimensional gel electrophoresis after elution and dialysis according to yet another aspect of the present invention.

Human off clot serum is filtered through a 0.45 micron filter to remove particulate matter capable of plugging chromatographic columns. A BIO-RAD MACROPREP HIGH Q® column (1 ml) is equilibrated in about 15-20 column volumes of 20 mM Na MES, pH 6.2 with 0.154M NaCl (normal saline). 8 ml of whole serum is added to 8 ml of 20 mM Na MES, pH6.2 with 0.154M NaCl. The sample mixture is adjusted to pH 6.2 with NaOH. The sample solution is pumped onto the column at a rate of 0.5 ml/min. The column effluent is collected as the flow-through unbound fraction. After application of the sample solution, the column is washed with 5 ml of column buffer (20 mM Na MES, pH 6.2 with 0.154M NaCl). The bound proteins are then eluted with 5 ml of 1M NaCl and are maintained separately from the flow-through fraction. FIG. 1 shows the flow-through or unbound fraction (left), molecular weight markers (middle), and the bound fraction (right). This figure demonstrates the separation that is achieved using the present techniques, and particularly the absence of high abundance proteins such as IgG, transferrin, and albumin from the bound fraction. FIG. 2 shows 100 ug of total protein from the unbound fraction following processing on a 2D 10% SDS gel.

Example 2

Figure 4:
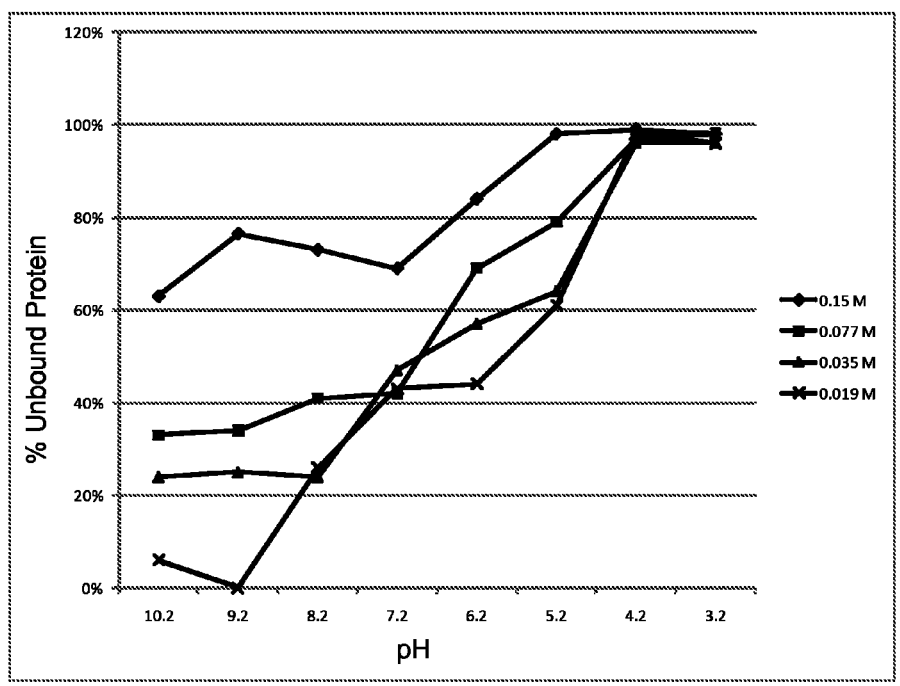
FIG. 4 is a graphical representation of bound vs. unbound protein at different pH and salt conditions according to a further aspect of the present invention.

The protocol of Example 1 is repeated to examine the proportion of protein bound to a column for a series of fixed pH and fixed NaCl concentrations. Buffers used to equilibrate the column at a fixed pH are shown in Table 1. A series of protein separations are run for each pH at varying NaCl concentrations, namely, 0.15M NaCl (normal saline), 0.077N NaCl (½ normal saline), 0.035M NaCl (¼ normal saline) and 0.019M (⅛ normal saline). The results for this series of experiments are shown in FIG. 4.

TABLE 1

| Fixed pH | Buffer |
|---|---|
| 3.2 | Sodium Formate |
| 4.2 | Sodium Citrate |
| 5.2 | Sodium Acetate |
| 6.2 | Sodium MES |
| 7.2 | Sodium Phosphate |
| 8.2 | Tris-HCl |
| 9.2 | Sodium Borate |
| 10.2 | Sodium Beta-alanine |

Example 3

The following protocol is used for the removal of high abundance proteins from a protein mixture using a cation-exchange column.

Human off clot serum is filtered through a 0.45 micron filter to remove particulate matter capable of plugging chromatographic columns. A BIO-RAD MACROPREP HIGH S® column (1 ml) is equilibrated in about 15-20 column volumes of 10 mM sodium citrate buffer (pH 4.2) with 0.019 M NaCl (1/8 normal saline). 0.25 ml of filtered (0.45 micron) serum is mixed with 0.75 ml of 10 mM sodium citrate buffer, and to the resulting mixture is added 2.0 ml of 10 mM sodium citrate buffer with 0.0195 M NaCL (1/8 normal saline) to form 3.0 ml of column sample. The sample is applied to the column that has been equilibrated in 10 mM sodium citrate buffer with 1/8 normal saline. The column effluent is collected as the flow-through unbound fraction. The column is washed with 5 ml of 10 mM sodium citrate buffer with 1/8 normal saline, and the bound proteins are then eluted with 5 ml of 1M NaCl and are maintained separately from the flow-through fraction. The preceding example thus provides effective removal of high abundance proteins from a protein mixture.

Example 4

The following protocol is used for the enrichment of urine proteins by anion-exchange chromatography. Large volumes of urine can be processed because protein content is low compared to serum. 50 ml of human urine is added to 5 ml of 20 mM sodium acetate (pH 5.2 adjusted with NaOH) to produce a 55 ml column sample. A BIO-RAD MACROPREP HIGH Q® column (1 ml) is equilibrated in about 15-20 column volumes of 20 mM sodium acetate (pH 5.2) with 0.077M NaCl (1/2 normal saline). The sample is applied to the column at a rate of 0.5 ml/min, and the column effluent is collected as the flow-through fraction. The column is washed with 5 ml of 20 mM sodium acetate (pH 5.2 with 0.077 M NaCl (1/2 normal saline), and the bound proteins are then eluted with 5 ml of 1M NaCl and are maintained separately from the flow-through fraction. The preceding example thus provides effective enrichment of urine proteins.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for isolating high abundant proteins from a high concentration protein mixture, comprising:
    delivering a high concentration protein mixture through an anion exchange column at a fixed pH and a fixed salt concentration, wherein the fixed pH and the fixed salt concentration have been preselected to cause separation of the protein mixture into a bound protein fraction and a flow-through protein fraction, wherein the bound protein fraction binds to the anion exchange column and the flow-through protein fraction flows though the anion exchange column without binding to the column, and wherein a majority of the high abundant proteins are in the flow-through protein fraction; and
    receiving the flow-through protein fraction containing the majority of the high abundant proteins from the anion exchange column separate from the bound protein fraction.

2. The method of claim 1, wherein the high abundant proteins include a plurality of proteins from the group consisting of transferrin, immunoglobulin, albumin, and fibrinogen.

3. The method of claim 1, wherein the fixed pH is from about 2.0 to about 10.0 and the fixed salt concentration is from about 2 mM to about 400 mM.

4. The method of claim 1, wherein the fixed pH is from about 5.2 to about 8.2 and the fixed salt concentration is from about 20 mM to about 300 mM.

5. The method of claim 1, wherein the bound protein fraction does not affinity bind to the anion exchange column.

6. The method of claim 1, wherein the fixed pH is less than or equal to about 7.0.

7. The method of claim 1, wherein the fixed pH is less than or equal to about 6.5.

8. The method of claim 1, wherein the fixed pH is from about 2.0 to about 6.0.

9. The method of claim 1, further comprising eluting the bound protein fraction from the anion exchange column.

10. The method of claim 1, wherein the high concentration protein mixture is a biological fluid.

11. The method of claim 10, wherein the biological fluid is selected from the group consisting of blood serum, blood plasma, urine, CNS fluid, saliva, cellular extracts, tissue culture extracts, and mixtures thereof.

12. The method of claim 10, wherein the high concentration protein mixture is an undiluted biological fluid.

13. The method of claim 10, wherein the high concentration protein mixture is a non-dialyzed biological fluid.

14. The method of claim 10, wherein the high concentration protein mixture is a non-ultafiltrated biological fluid.

15. The method of claim 1, wherein the anion exchange column has a protein capacity that is at least the same as the total protein in an undiluted protein mixture.

16. The method of claim 1, wherein the anion exchange column has a protein capacity that is at least 5 times smaller than the total protein in an undiluted protein mixture.

17. The method of claim 1, wherein the high concentration protein mixture has a protein concentration that is at least 10% greater than the anion exchange column protein capacity.

18. The method of claim 1, wherein the high concentration protein mixture has a protein concentration that is at least 20% greater than the anion exchange column protein capacity.

19. The method of claim 1, wherein greater than 50% of protein in the protein mixture is in the flow through fraction.

20. The method of claim 1, wherein greater than or equal to about 75% of protein in the protein mixture is in the flow through fraction.

* * * * *